United States Patent [19]

Post et al.

[11] 4,292,410

[45] Sep. 29, 1981

[54] PROCESS FOR THE PREPARATION OF HYDROCARBONS FROM SYNTHESIS GAS

[75] Inventors: Martin F. M. Post; Lambert Schaper, both of Amsterdam, Netherlands

[73] Assignee: Shell Oil Company, Houston, Tex.

[21] Appl. No.: 95,028

[22] Filed: Nov. 16, 1979

[30] Foreign Application Priority Data

Nov. 30, 1978 [NL] Netherlands ................. 7811735

[51] Int. Cl.$^3$ ............................................. C07C 1/04
[52] U.S. Cl. ........................... 518/714; 252/455 R; 518/728
[58] Field of Search ............. 260/449 R, 449.6, 449.5; 518/728, 714

[56] References Cited

U.S. PATENT DOCUMENTS

| | | | |
|---|---|---|---|
| 3,894,102 | 7/1975 | Chang et al. | 260/450 |
| 4,086,262 | 4/1978 | Chang et al. | 260/449.6 R |
| 4,096,163 | 6/1978 | Chang et al. | 260/449 R |
| 4,157,338 | 6/1979 | Hoag et al. | 260/449 R |
| 4,180,516 | 12/1979 | Chang et al. | 260/449 R |
| 4,188,336 | 2/1980 | Chang et al. | 260/449 M |

*Primary Examiner*—Howard T. Mars
*Attorney, Agent, or Firm*—Ronald R. Reper

[57] ABSTRACT

A process is disclosed for the preparation of an aromatic hydrocarbon mixture from a mixture of carbon monoxide and hydrogen using a mixture of two catalysts; one for the conversions of a $CO/H_2$ mixture into acyclic oxygen-containing hydrocarbons, and the other is a certain crystalline silicate having very high silica to alumina ratio, capable of catalyzing the conversion of acyclic oxygen-containing hydrocarbons into aromatic hydrocarbons.

8 Claims, No Drawings

PROCESS FOR THE PREPARATION OF HYDROCARBONS FROM SYNTHESIS GAS

BACKGROUND OF THE INVENTION

The invention relates to a process for the preparation of an aromatic hydrocarbon mixture from a mixture of carbon monoxide and hydrogen using a mixture of two catalysts of which one has the capability of catalysing the conversion of an $H_2/CO$ mixture into acyclic oxygen-containing hydrocarbons, and the other is a crystalline silicate which has the capability of catalysing the conversion of acyclic oxygen-containing hydrocarbons into aromatic hydrocarbons.

It is known to prepare aromatic hydrocarbons from synthesis gas over a mixture of a methanol synthesis catalyst and certain crystalline silicates, as disclosed in German patent application No. 2,518,097 and U.S. Pat. Nos. 4,086,267 and 4,096,163. However, for commercial application is highly desirable to employ a process wherein higher selectivity to products boiling in the gasoline range, i.e., pentanes and higher ($C_5^+$) is achieved.

In an investigation by Applicants concerning the above-mentioned process it was found that the catalyst mixtures show a higher $C_5^+$ selectivity according as, in the formula which shows the composition of the silicate, the value of y is lower. It was found that to reach a $C_5^+$ selectivity which is acceptable for commercial use of the process, y should be at most 0.005.

The invention therefore relates to a process for the preparation of an aromatic hydrocarbon mixture in which a mixture of carbon monoxide and hydrogen is contacted with a mixture of two catalysts of which one is capable of catalysing the conversion of an $H_2/CO$ mixture into acyclic oxygen-containing hydrocarbons, and the other is a crystalline silicate as defined hereinafter, of which in the formula giving the composition of the silicate, the value of y is at most 0.005.

SUMMARY OF THE INVENTION

According to the invention there is provided a process for the preparation of an aromatic hydrocarbon mixture, which comprises contacting a mixture of carbon monoxide and hydrogen is contacted at an elevated temperature and pressure with a mixture of two catalysts of which one is capable of catalysing the conversion of an $H_2/CO$ mixture into acyclic oxygen-containing hydrocarbons, and the other is a crystalline silicate, which silicate is characterized by having the following properties after 1 hour's calcining in air at 500° C.:
(a) thermally stable up to a temperature above 600° C.,
(b) an X-ray powder diffraction pattern showing, inter alia, the reflections given in Table A,

TABLE A

| Radiation: Cu-Ka 2 θ | Wavelength 0.15418 nm relative intensiyl |
|---|---|
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |

TABLE A-continued

| Radiation: Cu-Ka 2 θ | Wavelength 0.15418 nm relative intensiyl |
|---|---|
| 23.8–24.1 | VS |
| 24.2–24.8 | S |
| 29.7–30.1 | M | where the letters used have the following meanings: VS=very strong; S=strong; M=moderate; W=weak; θ=angle according to Bragg's law,
(c) after evacuation at $2 \times 10^{-9}$ bar and 400° C. for 16 hours and measured at a hydrocarbon pressure of $8 \times 10^{-2}$ bar and 100° C., the adsorption of n-hexane is at least 0.8 mmol/g, the adsorption of 2,2-dimethylbutane at least 0.5 mmol/g, and the ratio $$\frac{\text{adsorption of n-hexane}}{\text{adsorption of 2,2-dimethylbutane}}$$

at least 1.5,
(d) the composition, expressed in moles of the oxides, is as follows: $y.(1.0 \pm 0.3). M_2O.y.Al_2O_3.SiO_2$, where M=H and alkali metal and $0 < y \leq 0.005$.

DESCRIPTION OF PREFERRED EMBODIMENTS

The process according to the invention starts from an $H_2/CO$ mixture. Such a mixture can very conveniently be prepared by steam gasification of a carbon-containing material. Examples of such materials are brown coal, anthracite, coke, crude mineral oil and fractions thereof, and oils recovered from tar sand and bituminous shale. The steam gasification is preferably carried out at a temperature between 900° and 1500° C. and a pressure between 10 and 50 bar. In the process according to the invention the preferred starting material is an $H_2/CO$ mixture whose molar ratio is between 0.25 and 1.0.

The process according to the invention is preferably carried out at a temperature of 200°–500° C. and particularly of 300°–450° C., a pressure of 1–150 bar and particularly of 5–100 bar and a space velocity of 50–5000 and particularly of 300–3000 Nl gas/l catalyst/h.

In the process according to the invention a mixture of two catalysts is used, which, for the sake of convenience, will be designated catalysts X and Y. Catalyst X is the one which is capable of catalysing the conversion of an $H_2/CO$ mixture into acyclic oxygen-containing hydrocarbons and catalyst Y is the crystalline silicate. Catalysts that are preferably used as X-catalysts are those which are capable of converting an $H_2/CO$ mixture into substantially methanol and/or dimethyl ether. Very suitable for the present purpose are catalysts which contain zinc together with chromium. When using such a catalyst, it is preferred to choose one in which the atomic percentage of zinc, based on the sum of zinc and chromium, is at least 60% and in particular 60–80%. The catalyst mixture that is used in the process according to the invention may be a macromixture or a micromixture. In the first case the catalyst mixture consists of two kinds of macroparticles, of which one kind consists completely of catalyst X, and the other kind completely of catalyst Y. In the second case the catalyst mixture consists of one kind of macroparticles, each macroparticle being built up of a great number of microparticles of each of the catalysts X and Y. Catalyst mixtures in the form of micromixtures may be prepared, for instance, by thoroughly mixing a fine powder of catalyst X with a fine poder of catalyst Y and shaping the mixture into larger particles, for instance, by extruding or tabletting. In the process according to the invention it is preferred to use catalyst mixtures in the form of micromixtures. In view of the required activity of the catalyst mixtures, preferred mixtures are those containing per part by volume of catalyst Y, 1-5 parts by volume of catalyst X. The said crystalline silicates are characterized by having the following properties after 1 hour's calcining in air at 500° C.:

(a) thermally stable up to a temperature above 600° C.,
(b) an X-ray powder diffraction pattern showing, inter alia, the reflections given in Table A,

TABLE A

| Radiation: Cu-Ka<br>2θ | Wavelength 0.15418 nm<br>relative intensiyl |
| --- | --- |
| 7.8-8.2 | S |
| 8.7-9.1 | M |
| 11.8-12.1 | W |
| 12.4-12.7 | W |
| 14.6-14.9 | W |
| 15.4-15.7 | W |
| 15.8-16.1 | W |
| 17.6-17.9 | W |
| 19.2-19.5 | W |
| 20.2-20.6 | W |
| 20.7-21.1 | W |
| 23.1-23.4 | VS |
| 23.8-24.1 | VS |
| 24.2-24.8 | S |
| 29.7-30.1 | M | where the letters used have the following meanings: VS=very strong; S=strong; M=moderate; W=weak; θ=angle according to Bragg's law, (c) after evacuation at $2 \times 10^{-9}$ bar and 400° C. for 16 hours and measured at a hydrocarbon pressure of $8 \times 10^{-2}$ bar and 100° C., the adsorption of n-hexane is at least 0.8 mmol/g, the adsorption of 2,2-dimethylbutane at least 0.5 mmol/g, and the ratio $$\frac{\text{adsorption of n-hexane}}{\text{adsorption of 2,2-dimethylbutane}}$$

at least 1.5,
(d) the composition, expressed in moles of the oxides, is as follows: $y \cdot (1.0 \pm 0.3) \cdot M_2O \cdot y \cdot Al_2O_3 \cdot SiO_2$, where M=H and alkali metal and $0 < y \leq 0.005$.

The crystalline silicate that is present in the catalyst mixtures as catalyst Y, is defined, inter alia, with reference to the X-ray powder diffraction pattern shown by the silicate after 1 hour's calcining in air at 500° C. This X-ray powder diffraction pattern would contain, inter alia, the reflections shown in Table A. The complete X-ray powder diffraction pattern of a typical example of a silicate eligible for use according to the invention is shown in Table B (Radiation: Cu-Ka; wavelength: 0.15418 nm).

TABLE B

| 2θ | relative intensity<br>(100. I/Io) | description |
| --- | --- | --- |
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |
| 15.95 | 9 | BD |
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100[(x)] | SP |
| 23.95 | 45 | SP |
| 24.40 | 27 | SP |
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

[(x)]$I_o$ = intensity of the strongest separate reflection present in the pattern.

The letters used in Table B for describing the reflections have the following meanings: SP=sharp; SR=shoulder; NL=normal; BD=broad; O=angle according to Bragg's law.

The crystalline silicates which are used in the catalyst mixtures can be prepared from an aqueous mixture as the starting material which contains the following compounds: one or more compounds of an alkali metal (M), one or more compounds containing an organic cation (R) or from which such a cation is formed during the preparation of the silicate, one or more silicon compounds and one or more aluminum compounds. The preparation takes place by maintaining the mixture at elevated temperature until the silicate has been formed and subsequently separating the crystals of the silicate from the mother liquor. In the aqueous mixture from which the silicates are prepared, the various compounds should be present in the following molar ratio, expressed in moles of the oxides:
$M_2O:(R)_{2/n}O = 0.1-20$,
$(R)_2O:SiO_2 = 0.01-0.5$, and
$SiO_2:Al_2O_3 > 200$; n is the valency of R.

In the preparation of the silicates it is preferred to start from a basic mixture in which M is present in a sodium compound and R in a tetrapropylammonium compound.

In view of the required stability of the catalyst mixtures in the process according to the invention preference is given to silicates having an average crystallite size of less than 3000 nm and particularly of less than 1000 nm. The average crystallite size of the silicates can be adjusted with the aid of the molar ratio of $(R)_{2/n}O$ to $SiO_2$ in the starting mixture, in the sense that silicates with a lower average crystallite size are obtained according as the molar ratio of $(R)_{2/n}O$ to $SiO_2$ in the starting mixture is chosen higher.

In connection with the activity of the catalyst mixtures in the process according to the invention preference is given to silicates of which, in the formula which gives the composition of the silicate, the value of y is at least 0.002 and in particular at least 0.0025. Silicates of which y is at most 0.004 are preferred in view of the required stability of the catalyst mixtures. In the formula which gives the composition of the silicates, the value of y can be adjusted with the aid of the molar ratio of $SiO_2$ to $Al_2O_3$ in the starting mixture, in the sense that silicates with a lower value for y are obtained according as the molar ratio of $SiO_2$ to $Al_2O_3$ in the starting mixture is chosen higher.

The silicates prepared in the way described above contain alkali metal ions and organic cations. By using suitable exchange methods the alkali metal ions can be replaced by other cations, such as hydrogen ions or ammonium ions. Organic cations can be very suitably converted into hydrogen ions by calcining the silicates. The crystalline silicates which are used in the catalyst mixtures preferably have an alkali metal content of less than 1% w and particularly less than 0.05% w. If desired, a binder material such as bentonite or kaolin may be incorporated into the catalyst mixtures.

The process according to the invention can very suitably be carried out by conducting the feed in upward or downward direction through a vertically mounted reactor, in which a fixed or a moving bed of the catalyst mixture concerned is present. The process may, for instance, be carried out by conducting a feed in upward direction through a vertically mounted catalyst bed, using such a gas rate that expansion of the catalyst bed occurs. If desired, the process can also be carried out using a suspension of the catalyst mixture in a hydrocarbon oil. Depending on whether the process is carried out with a fixed catalyst bed, an expanded catalyst bed or a catalyst suspension, preference is given to catalyst particles with a diameter between 1 and 5 mm, 0.5 and 2.5 mm and 20 and 150 μm, respectively.

The invention will now be explained with reference to the following example.

EXAMPLE

A crystalline silicate (silicate A) was prepared as follows: A mixture of $SiO_2$, $Na_2AlO_2$, NaOH and $[(C_3H_7)_4N]OH$ in water with the molar composition $5Na_2O.Al_2O_3. 22.5[(C_3H_7)_4N]_2O. 125\ SiO_2. 2250\ H_2O$ was heated for 48 hours in an autoclave at 150° C. under autogenous pressure. After the reaction mixture had cooled down, the silicate formed was filtered off, washed with water until the pH of the wash water was about 8 and dried for two hours at 120° C. After 1 hour's calcining in air at 500° C. silicate A had the following properties:
(a) thermally stable up to a temperature above 800° C.;
(b) an X-ray powder diffraction pattern substantially equal to the one given in Table B;
(c) after evacuation for 16 hours at $2\times10^{-9}$ bar and 400° C. and measured at a hydrocarbon pressure of $8\times10^{-2}$ bar and 100° C., the adsorption of n-hexane is 1.2 mmol/g, the adsorption of 2,2-dimethylbutane 0.7 mmol/g and the ratio $$\frac{\text{adsorption of n-hexane}}{\text{adsorption of 2,2-dimethylbutane}} = 1.7,$$

and
(d) the composition, expressed in moles of the oxides, is $0.011\ M_2O.\ 0.011\ Al_2O_3.SiO_2$, where M=H and Na.

From silicate A, which had an average crystallite size of 280 nm, a silicate B was prepared by boiling the material calcined at 500° C. with 1.0 molar $NH_4NO_3$ solution, washing with water, boiling again with 1.0 molar $NH_4NO_3$ solution and washing, drying for 2 hours at 120° C. and calcining for 1 hour at 500° C.

A crystalline silicate (silicate C) was prepared in substantially the same way as silicate A, the difference being that for the preparation of silicate C the starting material was an aqueous mixture with the molar composition $16\ Na_2O.\ Al_2O_3.\ 72[(C_3H_7)_4N]_2O.\ 400\ SiO_2.\ 7200\ H_2O$. After 1 hour's calcining in air at 500° C. silicate C was completely equal to silicate A as regards thermal stability, X-ray powder diffraction pattern and adsorption behaviour. The composition of silicate C (after calcining), expressed in moles of the oxides, was as follows: $0.0035\ M_2O.\ 0.0035\ Al_2O_3.SiO_2$, where M=H and Na.

From silicate C, which had an average crystallite size of 240 nm, a silicate D was prepared in the same way as described above for the preparation of silicate B from silicate A.

Two catalyst mixtures (I and II) were prepared by mixing a $ZnO-Cr_2O_3$ composition with silicate B and silicate D, respectively. The atomic Zn percentage of the $ZnO-Cr_2O_3$ composition based on the sum of Zn and Cr was 70%. The catalyst mixtures both contained per part by volume of silicate, 2.4 parts by volume of the $ZnO-Cr_2O_3$ composition.

Catalyst mixture I (prepared with silicate B) and catalyst mixture II (prepared with silicate D) were tested for the one-step preparation of an aromatic hydrocarbon mixture from an $H_2/CO$ mixture. The testing was carried out in a 50-ml reactor in which a fixed catalyst bed with a volume of 7.5 ml was present. An $H_2/CO$ mixture with an $H_2/CO$ molar ratio of 0.5 was conducted for 48 hours at a temperature of 375° C., a pressure of 60 bar and a space velocity of 1000 $1.1^{-1}.h^{-1}$ over the catalyst. The results of these experiments are given below:

| Experiment No. | 1 | 2 |
| --- | --- | --- |
| Catalyst mixture No. | I | II |
| Average composition of the $C_1^+$ product, % W | | |
| $C_1$ | 4 | 5 |
| $C_2$ | 5 | 8 |
| $C_3$ | 27 | 12 |
| $C_4$ | 8 | 5 |
| $C_5^+$ | 56 | 70 |
| Average composition of the $C_5^+$ product, % W | | |
| acyclic hydrocarbons | 19 | 19 |
| napththenes | 7 | 17 |
| aromatics | 74 | 64 |

What is claimed is:

1. In a process for the preparation of a hydrocarbon mixture of pentanes and higher and containing aromatics, which process comprises contacting a mixture of carbon monoxide and hydrogen at an elevated temperature and pressure with a catalyst mixture consisting essentially of two catalysts, a catalyst X being capable of catalysing the conversion of an $H_2/CO$ mixture into substantially methanol and/or dimethyl ether, and containing zinc together with chromium, and a catalyst Y, which is a crystalline silicate, which silicate is characterized by having the following properties after 1 hour's calcining in air at 500° C.:
(a) thermally stable up to a temperature above 600° C.,
(b) an X-ray powder diffraction pattern showing, inter alia, the reflections given in Table A:

TABLE A

| Radiation: Cu-Ka | Wavelength 0.15418 nm |
|---|---|
| 2θ | relative intensiyl |
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | where the letters used have the following meanings:
VS=very strong; S=strong; M=moderate, W=weak; θ=angle according to Bragg's law.

(c) after evacuation at $2 \times 10^{-9}$ bar and 400° C. for 16 hours and measured at a hydrocarbon pressure of $8 \times 10^{-2}$ and 100° C., and adsorption of n-hexane is at least 0.8 mmol/g, the adsorption of 2,2-dimethylbutane at least 0.5 mmol/g, and the ratio $$\frac{\text{adsorption of n-hexane}}{\text{adsorption of 2,2-dimethylbutane}}$$

at least 1.5

(d) the composition, expressed in moles of the oxides, is as follows: y.(1.0±0.3). $M_2O.y.Al_2O_3.SiO_2$, where M=H and alkali metal, the improvement comprising $0.0020 < y \leq 0.0040$.

2. A process according to claim 1, wherein the molar ratio of hydrogen to carbon monoxide in the feed is between 0.25 and 1.0.

3. A process according to claim 1, wherein it is carried out at a temperature in the range of 200°–500° C., a pressure in the range of 1–150 bar and a space velocity in the range of 50–5000 Nl gal/l catalyst/h.

4. A process according to claim 3, wherein it is carried out at a temperature of 300°–450° C., a pressure of 5–100 bar and a space velocity of 300–3000 Nl gas/l catalyst/h.

5. A process according to claim 1, wherein in the X-catalyst the atomic percentage of zinc, based on the sum of zinc and chromium, is 60–80%.

6. A process according to claim 1, wherein the catalyst mixture contains 1–5 parts by volume of catalyst X per part by volume of catalyst Y.

7. A process according to claim 1, wherein the catalyst mixture contains a crystalline silicate whose average crystallite size is less than 3000 nm.

8. A process according to claim 1, wherein in the catalyst mixture the crystalline silicate component has an alkali metal content of less than 0.05% w.

* * * * *